United States Patent
Ogawa et al.

(10) Patent No.: US 7,504,256 B1
(45) Date of Patent: Mar. 17, 2009

(54) PROCESS FOR PRODUCING POLYPEPTIDE

(75) Inventors: Tatsuya Ogawa, Hofu (JP); Yoshinobu Konno, Machida (JP); Naohisa Akashi, Hofu (JP); Hiroshi Takasugi, Machida (JP); Seiji Sugimoto, Machida (JP); Keiichi Yano, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 262 days.

(21) Appl. No.: 10/110,997

(22) PCT Filed: Oct. 19, 2000

(86) PCT No.: PCT/JP00/07288

§ 371 (c)(1),
(2), (4) Date: Apr. 19, 2002

(87) PCT Pub. No.: WO01/29246

PCT Pub. Date: Apr. 26, 2001

(30) Foreign Application Priority Data

Oct. 19, 1999 (JP) .................................. 11-296267

(51) Int. Cl.
  C12N 5/06 (2006.01)
  C12N 5/12 (2006.01)
  C12N 5/16 (2006.01)
(52) U.S. Cl. ..................... 435/374; 435/375; 435/383; 435/387
(58) Field of Classification Search .................. 435/374, 435/375, 355, 383, 384, 388, 389
  See application file for complete search history.

(56) References Cited

U.S. PATENT DOCUMENTS

| | | | | |
|---|---|---|---|---|
| 4,350,683 A | * | 9/1982 | Galfre et al. ................. | 435/449 |
| 4,757,018 A | | 7/1988 | Brown | |
| 4,849,509 A | * | 7/1989 | Thurin et al. ............ | 530/388.2 |
| 5,614,385 A | | 3/1997 | Oppermann et al. | |
| 5,658,789 A | | 8/1997 | Quaranta et al. | |
| 5,672,502 A | | 9/1997 | Birch et al. | |
| 5,830,470 A | * | 11/1998 | Nakamura et al. ....... | 424/133.1 |

FOREIGN PATENT DOCUMENTS

| | | | |
|---|---|---|---|
| EP | 0 292 965 A2 | | 11/1988 |
| EP | 481791 A2 | | 4/1992 |
| EP | 0 625 574 A1 | | 11/1994 |
| EP | 811691 | * | 12/1997 |
| JP | 9-49836 A | | 2/1997 |
| JP | 11-127890 A | | 5/1999 |
| WO | 86/05807 A1 | | 10/1986 |
| WO | WO 86/05807 | * | 10/1986 |
| WO | 97/33978 A1 | | 9/1997 |

OTHER PUBLICATIONS

Ozturk et al (Journal of Biotechnology, 1990, vol. 16, pp. 259-278).*
Broad and Rhodes (Cytotechnology, 1991, vol. 5, pp. 47-55).*
Stevenson et al; "Rat Carcinoma Calls in Long-Term. Serum-Free Culture Provide a Continuing Supply of Collagenase", Bioscience Reports, Dec. 1985, vol. 5, No. 12, pp. 1071-1077.
Atkinson et al; "Production of Somatomedin-Like Activity by Human Adult Tumor-Derived, Transformed, and Normal Cell Cultures and Bycultured Rat Hepatocytes: Effects of Culture Conditions and of Epidermal Growth Factor (Urogastrone)"; Canadian Jounral of Biochemistry and Cell Biology, Dec. 1984, vol. 62, No. 12, pp. 1343-1350.
Keen, M.J.; "The Culture of Rat Myeloma and Rat Hybridoma Cells in a Protein-Free Medium"; Biology Research Division , UK, Jun. 8, 1995, vol. 17, pp. 193-202.
Bibila, et al; "Monoclonal Antibody Process Development Using Medium Concentrates";Biotechnol. Prog., 1994,vol. 10, No. 1, pp. 87-96.
Castro et al; "Cho Cell Growth and Recombinant Interferon-Y Production: Effects of BSA, Pluronic and Lipids"; Reseach School of Biosciences, UK, Aug. 30, 1995, vol. 19, pp. 27-36.
Environmental Conditions for Cell Growth; pp. 2C:0.1-2C:2.6.
Rasmussen et al., Cytotechnology, vol. 28, 1998, pp. 31-42.
Zhou et al., Cytotechnology, vol. 22, No. 1-3, 1996, pp. 239-250.
Shitara et al., Journal of Immunological Methods, vol. 167, No. 1/2, 1994, pp. 271-278.
Zhou et al., Biotechnology and Bioengineering, vol. 55, No. 5, 1997, pp. 783-792.
Berg et al., Biotechniques, vol. 14, No. 6, 1993, pp. 972-978.
Supplementary European Search Report dated Apr. 18, 2005 issued in EP 00 96 9908.
Office Action dated Jul. 30, 2007 issued in connection with EP 00 969 908.3.
Kim et al, "Growth and Differentation of Rat Mammary Epithelial Cells Cultured in Serum-free Medium", Arch. Pharm. Res., vol. 20, No. 4, pp. 297-305, 1997.

* cited by examiner

*Primary Examiner*—Karen A Canella
(74) *Attorney, Agent, or Firm*—Sughrue Mion, PLLC

(57) ABSTRACT

The present invention relates to a process for producing a desired polypeptide using rat cells. Specifically, the present invention relates to a process for producing the polypeptide which comprises culturing rat cells such as YB2/3HL.P2.G11.16Ag.20 (hereinafter referred to as YB2/0), preferably rat cells to which a recombinant DNA comprising DNA encoding a desired polypeptide such as an immunologically functional molecule is introduced, in a medium which does not contain serum (hereinafter referred to as a serum-free medium). Among the desired polypeptides obtained by the process of the present invention, an antibody obtained by using a transformant of YB2/0 has a high antibody-dependent cell-mediated cytotoxic activity (hereinafter sometimes referred to as ADCC activity) and is useful as a pharmaceutical agent.

18 Claims, 3 Drawing Sheets

PROCESS FOR PRODUCING POLYPEPTIDE

This application is the US national phase of international application PCT/JP00/07288 filed 19 Oct. 2000, which designated the US.

TECHNICAL FIELD

The present invention relates to a process for producing desired a polypeptide using rat cells. Specifically, the present invention relates to a process for producing the polypeptide which comprises culturing rat cells such as YB2/3HL.P2.G11.16Ag.20 (hereinafter referred to as YB2/0), preferably rat cells to which a recombinant DNA comprising DNA encoding a desired polypeptide such as an immunologically functional molecule is introduced, in a medium which does not contain serum (hereinafter referred to as a serum-free medium). Among the desired polypeptides obtained by the process of the present invention, an antibody obtained by using a /transformant of YB2/0 has a high antibody-dependent cell-mediated cytotoxic activity (hereinafter sometimes referred to as ADCC activity) and is useful as a pharmaceutical agent.

BACKGROUND ART

Polypeptides having immunological functions such as antibodies have been found to be suitable for various pharmaceutical uses. For instance, they are utilized for the alleviation of rejection reaction to renal transplantation and in pharmaceuticals as antiviral agents for RSV infection in infants and as anti-cancer agents for breast cancer. It is expected that the use of antibody-containing pharmaceutical agents will be increasingly important.

Production of an antibody using a gene encoding the antibody is carried out by culturing recombinant cells comprising a vector to which a gene encoding the antibody is introduced and then recovering the antibody produced in the culture. Such recombinant antibodies are produced in their complete form only by animal cells, and therefore, it is preferred to use animal cells for the production of recombinant antibodies.

Production of useful substances using animal cells or recombinant animal cells is widely carried out for research and industrial purposes. In a process for producing a substance by culturing animal cells, culturing is usually carried out in a medium which contains serum. However, the presence of serum is liable to cause differences among batches, which considerably affect the yield of cells and the production of substances. Therefore, use of a medium which does not contain serum is desirable in the culturing of animal cells for the production of substances.

A process of culturing the rat myeloma cell line YB2/3.0Ag30 (hereinafter referred to as Y0) in a protein-free medium is known [Cytotechnology, 17, 193 (1995)]. Also known are processes for producing polypeptides by culturing animal cells in serum-free media [Biotechnol. Prog., 10, 87 (1994); Cytotechnology, 19, 27 (1996); Japanese Published Unexamined Patent Application No. 70757/94] and a process for producing polypeptides by inoculating into a serum-free medium transformed rat cells grown in a medium containing serum and then culturing the cells in the serum-free medium (PCT National Publication No. 502377/87).

However, there has been no report on a process for producing desired polypeptides stably for a long period of time using rat cells adapted to a serum-free medium.

As a culturing method for animal cells, batch culture is mainly employed. In the batch culture, cells are inoculated into a fresh medium and cultured therein for a certain period of time. It is known that when animal cells are cultured by batch culture, the cell growth rate and the productivity of polypeptide are low because of marked deterioration in culturing conditions during the culturing, e.g., exhaustion of nutrients and accumulation of waste matters from cells. This leads to a lowering of the polypeptide concentration in the culture, thereby raising the relative concentrations of protein components other than the desired polypeptide in the culture, such as proteins derived from cells or medium. As a result, steps for separating and purifying the polypeptide become tedious and production costs are increased, which makes the process disadvantageous.

DISCLOSURE OF THE INVENTION

An object of the present invention is to provide a process for efficiently producing a desired polypeptide using rat cells.

The present invention relates to the following (1) to (24).

(1) A process for producing a polypeptide which comprises culturing in a serum-free medium a rat cell line adapted to a serum-free medium, and recovering the desired polypeptide from the culture.

(2) The process according to (1), wherein the rat cell line adapted to a serum-free medium is a rat cell line which can be subcultured in a serum-free medium for two months or more.

(3) The process according to (1) or (2), wherein the rat cell is a myeloma cell or a hybrid cell derived from a myeloma cell.

(4) The process according to (1) or (2), wherein the rat cell is YB2/0.

(5) The process according to any one of (1) to (4), wherein the cell is a cell to which a recombinant DNA comprising DNA encoding the desired polypeptide is introduced.

(6) The process according to any one of (1) to (5), wherein the culturing is carried out by batch culture, fed-batch culture or perfusion culture.

(7) The process according to any one of (1) to (6), comprising adding at least one member selected from the group consisting of a nutrient factor and a physiologically active substance to the medium during the culturing.

(8) The process according to (7), wherein the nutrient factor is at least one member selected from the group consisting of glucose, an amino acid and a vitamin.

(9) The process according to (7), wherein the physiologically active substance is at least one member selected from the group consisting of insulin, transferrin and albumin.

(10) The process according to any one of (1) to (9), wherein the desired polypeptide is an immunologically functional molecule.

(11) The process according to (10), wherein the immunologically functional molecule is a protein or a peptide.

(12) The process according to (11), wherein the protein or peptide is an antibody, an antibody fragment or a fusion protein comprising an antibody Fc region.

(13) The process according to (12), wherein the antibody is an antibody recognizing a tumor-related antigen, an antibody recognizing an allergy- or inflammation-related antigen, an antibody recognizing a circulatory disease-related antigen, an antibody recognizing an autoimmune disease-related antigen, or an antibody recognizing a viral or bacterial infection-related antigen.

(14) The process according to (13), wherein the antibody recognizing a tumor-related antigen is an anti-GD2 antibody, an anti-GD3 antibody, an anti-GM2 antibody, an anti-HER2 antibody, an anti-CD52 antibody, an anti-MAGE antibody, an anti-basic fibroblast growth factor antibody, an anti-basic fibroblast growth factor receptor antibody, an anti-FGF8 antibody, an anti-FGF8 receptor antibody, an anti-insulin-like growth factor antibody, an anti-PMSA antibody, an anti-vascular endothelial cell growth factor antibody, or an anti-vascular endothelial cell growth factor receptor antibody; the antibody recognizing an allergy- or inflammation-related antigen is an anti-interleukin 6 antibody, an anti-interleukin 6 receptor antibody, an anti-interleukin 5 antibody, an anti-interleukin 5 receptor antibody, an anti-interleukin 4 antibody, an anti-interleukin 4 receptor antibody, an anti-tumor necrosis factor antibody, an anti-tumor necrosis factor receptor antibody, an anti-CCR4 antibody, an anti-chemokine antibody, or an anti-chemokine receptor antibody; the antibody recognizing a circulatory disease-related antigen is an anti-GpIIb/IIIa antibody, an anti-platelet-derived growth factor antibody, an anti-platelet-derived growth factor receptor antibody, or an anti-blood coagulation factor antibody; the antibody recognizing an autoimmune disease-related antigen is an anti-auto-DNA antibody; and the antibody recognizing a viral or bacterial infection-related antigen is an anti-gp120 antibody, an anti-CD4 antibody, an anti-CCR4 antibody, or an anti-verotoxin antibody.

(15) The process according to (13), wherein the antibody is an anti-GD3 human chimeric antibody, a humanized anti-interleukin 5 receptor a chain antibody, or an anti-GM2 human CDR-grafted antibody.

(16) The process according to any one of (1) to (15), wherein the rat cell is cultured while an insulin concentration in the culture kept is at 10 mg/l or above, followed by culturing while an insulin concentration in the culture is kept at 10 mg/l or below.

(17) A process for adapting a rat cell to a serum-free medium, which comprises inoculating rat cells into a conditioned medium at a cell density of $1 \times 10^5$ to $1 \times 10^6$ cells/ml.

(18) The process according to (17), wherein the rat cell is a myeloma cell or a hybrid cell derived from a myeloma cell.

(19) The process according to (17), wherein the rat cell is YB2/0.

(20) The process according to any one of (17) to (19), wherein the cell carries an introduced recombinant DNA comprising DNA encoding the desired polypeptide.

(21) A process for producing a rat cell line adapted to a serum-free medium, which comprises adapting rat cells to a serum-free medium by the process according to any one of (17) to (20), and then cloning the cells.

(22) A rat cell line adapted to a serum-free medium, which is obtained by the process according to (21).

(23) The rat cell line adapted to a serum-free medium according to (22), wherein the rat cell line is a rat cell line which can be subcultured in a serum-free medium for two months or more.

(24) A rat cell line adapted to a serum-free medium, 61-33γ (FERM BP-7325).

The cells of the present invention may be any rat cells and are preferably those to which a recombinant DNA comprising DNA encoding a desired polypeptide is introduced. Preferred rat cells are myeloma cells and hybrid cells derived from myeloma cells, e.g., Y3 Ag1.2.3. (ATCC CRL 1631), Y0 (ECACC No:85110501) and YB2/0 (ATCC CRL 1662). The cells of the present invention also include cells which are obtained by subjecting the above cells to mutagenesis or cell fusion with B cells obtained by immunization of a non-human mammal with an antigen and which have the same properties as the above cells.

The desired polypeptides of the present invention are preferably eucaryotic cell polypeptides, more preferably mammal cell polypeptides. The eucaryotic cell polypeptides may be artificially modified polypeptides such as fusion polypeptides or partial fragments thereof, so far as a eucaryotic cell polypeptide is contained as a part thereof.

The polypeptides of the present invention include immunologically functional molecules such as antibodies, biocatalyst molecules such as enzymes, and structure-forming and retaining molecules such as structural proteins. Preferred polypeptides are immunologically functional molecules.

The immunologically functional molecules may be any polypeptides such as proteins and peptides that relate to immune reactions in vivo. Examples of the immunologically functional molecules include interferon molecules such as interleukin-2 (IL-2) [Science, 193, 1007 (1976)] and interleukin-12 (IL-12) [J. Leuc. Biol., 55, 280 (1994)]; colony-stimulating factors such as granulocyte colony stimulating factor (G-CSF) [J. Biol. Chem., 258, 9017 (1983)], macrophage colony stimulating factor (M-CSF) [J. Exp. Med., 173, 269 (1992)] and granulocyte-macrophage colony stimulating factor (GM-CSF) [J. Biol. Chem., 252, 1998 (1977)]; and growth factors such as erythropoietin (EPO) [J. Biol. Chem., 252, 5558 (1977)] and thrombopoietin (TPO) [Nature, 369, 533 (1994)].

An antibody is a protein which is produced in vivo by an immune reaction caused by stimulation with an exogenous antigen and which has the activity to specifically bind to an antigen.

The antibodies include antibodies secreted from hybridomas prepared from spleen cells of an animal immunized with an antigen, and antibodies prepared by recombinant DNA techniques, i.e. antibodies produced by cells obtained by introducing an antibody-expressing vector carrying a gene encoding the antibody into host cells. Concretely, the antibodies include those produced by hybridomas, humanized antibodies and human antibodies.

A hybridoma is a cell which is obtained by fusing a B cell obtained from a non-human mammal immunized with an antigen with a rat-derived myeloma cell and which produces a monoclonal antibody having the desired antigenic specificity.

The humanized antibodies include human chimeric antibodies and human complementarity determining region (hereinafter referred to as CDR)-grafted antibodies.

A human chimeric antibody is an antibody comprising a heavy-chain variable region (hereinafter, the heavy chain and the variable region may be respectively referred to as H-chain and V region, and thus the antibody heavy-chain variable region may be referred to as HV or VH) and a light-chain variable region (hereinafter, the light chain may be referred to as L-chain and thus the region may be referred to as LV or VL) of an antibody derived from a non-human animal, a heavy-chain constant region (hereinafter, the constant region may be referred to as C region and thus this region may be referred to as CH) of a human antibody and a human light-chain constant region (hereinafter this region may be referred to as CL) of a human antibody. As the non-human animal, any animal can be used so far as hybridomas can be prepared from the animal. Suitable animals include mouse, rat, hamster and rabbit.

The human chimeric antibodies can be prepared by recovering cDNAs encoding VH and VL from a hybridoma which produces a monoclonal antibody, inserting the cDNAs into an expression vector comprising genes encoding human antibody CH and human antibody CL for a host cell to construct a human chimeric antibody expression vector, and introducing the vector into the host cell to express the antibody.

As the CH for the human chimeric antibodies, any CH of antibodies belonging to human immunoglobulin (hereinafter referred to as hIg) may be used. Preferred are those of antibodies belonging to the hIgG class, which may be of any subclass, e.g., hIgG1, hIgG2, hIgG3 and hIgG4. As the CL for the human chimeric antibodies, any CL of antibodies belonging to hIg, e.g., class κ or class λ, may be used.

A human CDR-grafted antibody is an antibody prepared by grafting the amino acid sequences of the CDR in the VH and VL of an antibody derived from a non-human animal into appropriate positions in the VH and VL of a human antibody.

The human CDR-grafted antibodies can be prepared by constructing cDNAs encoding V regions wherein the CDR sequences of the VH and VL of an antibody derived from a non-human animal are grafted into the CDR sequences of the VH and VL of an optional human antibody, inserting the resulting cDNAs into an expression vector comprising genes encoding human antibody CH and human antibody CL for a host cell to construct a human CDR-grafted antibody expression vector, and introducing the expression vector into the host cell to express the human CDR-grafted antibody.

As the CH for the human CDR-grafted antibodies, any CH of antibodies belonging to hIg may be used. Preferred are those of antibodies belonging to the hIgG class, which may be of any subclass, e.g., hIgG1, hIgG2, hIgG3 and hIgG4. As the CL for the human CDR-grafted antibodies, any CL of antibodies belonging to hIg, e.g., class κ or class λ, may be used.

The immunologically functional molecules include human chimeric antibodies, humanized antibodies and single chain antibodies. Examples of such antibodies include antibodies against ganglioside GD3 (hereinafter referred to as anti-GD3 antibodies) and antibodies against human interleukin-5 receptor α-chain (hereinafter referred to as anti-IL-5 receptor α-chain antibodies). An example of the anti-GD3 antibodies is anti-ganglioside GD3 human chimeric antibody (hereinafter referred to as anti-GD3 chimeric antibody) KM-871 (Japanese Published Unexamined Patent Application No. 304989/93), and examples of the anti-IL-5 receptor α-chain antibodies are humanized anti-IL-5 receptor α-chain antibody KM8399 (WO 97/10354) and anti-GM2 human CDR-grafted antibodies KM8966, KM8967, KM8969 and KM8970 (Japanese Published Unexamined Patent Application No. 257893/98).

As the DNA encoding the desired polypeptide, any DNA capable of expressing the polypeptide can be used. Preferred are DNAs encoding the immunologically functional molecules.

Examples of the expression vectors used in preparing the recombinant vector comprising the DNA encoding the desired polypeptide include pcDNAI, pcDM8 (manufactured by Funakoshi, Co., Ltd.), pAGE107 [Japanese Published Unexamined Patent Application No. 22979/91; Cytotechnology, 3, 133 (1990)], pAS3-3 (Japanese Published Unexamined Patent Application No. 227075/90), pCDM8 [Nature, 329, 840 (1987)], pcDNAI/Amp (manufactured by Invitrogen Corporation), pREP4 (manufactured by Invitrogen Corporation), pAGE103 [J. Biochem., 101, 1307 (1987)] and pAGE210.

As the promoter, any promoters capable of functioning in the animal cells used in the present invention can be used. Suitable promoters include the promoter of IE (immediate early) gene of cytomegalovirus (CMV), SV40 early promoter, the promoter of a retrovirus, metallothionein promoter, heat shock promoter, SR α promoter, etc. The enhancer of IE gene of human CMV may be used in combination with the promoter.

As the host cell, any rat cells may be used. Preferred rat cells are myeloma cells and hybrid cells derived from myeloma cells, e.g., Y3 Ag1.2.3., Y0 and YB2/0. The cells of the present invention also include cells which are obtained by subjecting the above cells to mutagenesis or cell fusion with B cells obtained by immunization of a non-human mammal with an antigen and which have the same properties as the above cells.

Introduction of the recombinant vector into rat cells can be carried out by any of the methods for introducing DNA into the cells, for example, electroporation [Cytotechnology, 3, 133 (1990)], the calcium phosphate method (Japanese Published Unexamined Patent Application No. 227075/90) and lipofection [Proc. Natl. Acad. Sci. USA, 84, 7413 (1987); Virology, 52, 456 (1973)].

By culturing the cells to which the recombinant vector is introduced by the above method in an appropriate medium, the desired polypeptide can be produced in the cells or in the culture supernatant.

Examples of the cells of the present invention include transformant 7-9-51 (FERM BP-6691) producing anti-GD3 human chimeric antibody, transformant KM7399 (FERM BP-5649) producing anti-IL-5 receptor α-chain chimeric antibody, transformant KM9399 (FERM BP-5647) producing anti-IL-5 receptor α-chain human CDR-grafted antibody, and transformants KM8966 (FERM BP-5105), KM8967 (FERM BP-5106), KM8969 (FERM BP-5527) and KM8970 (FERM BP-5528) producing anti-GM2 human CDR-grafted antibodies.

Adaptation of cells to a serum-free medium in accordance with the present invention can be carried out, for example, by adapting rat cells subcultured in a serum-containing medium directly to a commercially available serum-free medium, or by continuous adaptation (Cell & Tissue Culture Laboratory Procedures, JOHN WILEY & SONS 2C:1).

During the process of adaptation to a serum-free medium, the viability of cells lowers temporarily, which sometimes causes extinction of cells. Therefore, it is preferred to inoculate cells into a medium for the adaptation to a serum-free medium at a cell density of $1 \times 10^5$ to $10 \times 10^5$ cells/ml, preferably $4 \times 10^5$ to $6 \times 10^5$ cells/ml, in order to restore the viability of cells or to keep it high. In one embodiment according to the direct adaptation method, cells are inoculated into a medium and cultured by an ordinary culturing method for animal cells, e.g., batch culture in a 5% $CO_2$ incubator at 37° C. until the cell density reaches $10 \times 10^5$ to $40 \times 10^5$ cells/ml and then the cells are inoculated into a serum-free medium, followed by repetition of culturing under similar conditions.

The rat cells are inoculated into a serum-free medium at a density of $1 \times 10^5$ to $10 \times 10^5$ cells/ml, preferably $4 \times 10^5$ to $6 \times 10^5$ cells/ml, and cultured by an ordinary culturing method for animal cells. After 4 to 7 days of culturing, the rat cells whose density reached $10 \times 10^5$ to $40 \times 10^5$ cells/ml are selected as the cells adapted to a serum-free medium.

The cells adapted to a serum-free medium are inoculated into a medium employed in the batch culture described below at a density of $10 \times 10^5$ to $30 \times 10^5$ cells/ml and cultured for 3 to 5 days under the culturing conditions employed in the batch culture described below, whereby subculturing can be carried out. During the subculturing, it is preferred to maintain the viability of the cells adapted to a serum-free medium at 90% or more. In order to maintain the productivity of the desired polypeptide by the rat cells, e.g. YB2/0 and transformants of YB2/0, adapted to a serum-free medium, it is desirable to add albumin to a serum-free medium in an amount of 0.1 to 10 μl, preferably 0.5 to 3 g/l.

After the cells of the present invention are adapted to a serum-free medium, a cloned cell line can be prepared by using the limiting dilution method with a 96-well plate, the colony forming method, or the like.

Described below is a process for preparing a cloned cell line by the limiting dilution method.

A cell suspension is diluted and inoculated into wells in such an amount that the number of cells per well is not more than one, and culturing is carried out in a 5% $CO_2$ incubator at 30 to 40° C. using a commercially available serum-free medium or the like for several weeks. After the completion of culturing, the concentration of the desired polypeptide in the culture supernatant of the cells observed to have grown is determined, and the cells having a high productivity of the polypeptide are selected.

Cloning by the colony forming method can be carried out in the following manner.

In the case of adherent cells, a cell suspension is diluted and the cells are inoculated into a Petri dish and cultured. After the colony formation is confirmed, the colony is separated using a ring of a penicillin cap or the like, and the cells are released with an enzyme such as trypsin and then transferred into an appropriate incubator. The amount of the desired polypeptide produced is determined, and the cells having a high productivity of the polypeptide are selected.

In the case of suspending cells, a cell suspension is diluted and the cells are inoculated into soft agar and cultured. The formed colony is picked up under a microscope and then subjected to static culture. The amount of the desired polypeptide produced is determined, and the cells having a high productivity of the polypeptide are selected.

By repeating the above procedure, a cloned rat cell line adapted to a serum-free medium and having the desired cell characteristics can be selected.

According to the above process, a rat cell line adapted to a serum-free medium, preferably a rat cell line which can be subcultured in a serum-free medium for two months or more, can be obtained. A rat cell line which can be subcultured in a serum-free medium for two months or more is desirable for culturing cells adapted to a serum-free medium for a long period of time.

The rat cell line adapted to a serum-free medium can be subcultured by the above method for subculturing the cells adapted to a serum-free medium. An example of such rat cell line adapted to a serum-free medium is 61-33γ (FERM BP-7325).

Culturing of the cells of the present invention can be carried out by any of general culturing methods for animal cells capable of efficiently producing the desired polypeptides, for example, batch culture, repeated batch culture, fed-batch culture and perfusion culture. Preferably, fed-batch culture or perfusion culture is employed in order to raise the productivity of the desired polypeptides.

1. Batch Culture

The serum-free medium used in the process of the present invention is a medium prepared by adding, instead of serum, various physiologically active substances and nutrient factors, as well as carbon sources, nitrogen sources, etc. which can be assimilated by animal cells, to an ordinary basal medium employed for the culturing of animal cells.

Examples of suitable media include RPMI1640 medium [The Journal of the American Medical Association, 199, 519 (1967)], Eagle's MEM [Science, 122, 501 (1952)], Dulbecco's modified MEM [Virology, 8, 396 (1959)], 199 medium [Proceeding of the Society for the Biological Medicine, 73, 1 (1950)], F12 medium [Proc. Natl. Acad. Sci. USA, 53, 288 (1965)] and IMDM [J. Experimental Medicine, 147, 923 (1978)]. Preferred are DMEM, F12 medium and IMDM.

To the serum-free medium are added nutrient factors, physiologically active substances, etc. required for the growth of animal cells according to need prior to the culturing.

The nutrient factors include glucose, amino acids and vitamins.

Examples of the amino acids are L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine, which may be used alone or in combination.

Examples of the vitamins are d-biotin, D-pantothenic acid, choline, folic acid, myo-inositol, niacinamide, pyridoxal, riboflavin, thiamine, cyanocobalamin and DL-α-tocopherol, which may be used alone or in combination.

The physiologically active substances include insulin, transferrin and albumin.

As for the concentrations of the nutrient factors, glucose is added to give a concentration of 200 to 6000 mg/l, preferably 3000 to 5000 mg/l.

The amino acids are added, for example, to give the following concentrations: L-alanine, 1 to 160 mg/l (preferably 3 to 120 mg/l); L-arginine monohydrochloride, 10 to 1000 mg/l (preferably 30 to 800 mg/l); L-asparagine monohydrate, 10 to 200 mg/l (preferably 20 to 150 mg/l); L-aspartic acid, 5 to 100 mg/l (preferably 10 to 75 mg/l); L-cystine dihydrochloride, 10 to 200 mg/l (preferably 20 to 150 mg/l); L-glutamic acid, 5 to 200 mg/l (preferably 10 to 150 mg/l); L-glutamine, 50 to 2000 mg/l (preferably 100 to 1500 mg/l); glycine, 2 to 100 mg/l (preferably 5 to 75 mg/l); L-histidine monohydrochloride dihydrate, 5 to 200 mg/l (preferably 10 to 150 mg/l); L-isoleucine, 2 to 300 mg/l (preferably 4 to 200 mg/l); L-leucine, 5 to 300 mg/l (preferably 10 to 200 mg/l); L-lysine monohydrochloride, 10 to 300 mg/l (preferably 20 to 250 mg/l); L-methionine, 5 to 100 mg/l (preferably 10 to 75 mg/l); L-phenylalanine, 5 to 200 mg/l (preferably 10 to 150 mg/l); L-proline, 5 to 200 mg/l (preferably 10 to 150 mg/l); L-serine, 5 to 200 mg/l (preferably 10 to 150 mg/l); L-threonine, 5 to 200 mg/l (preferably 10 to 150 mg/l); L-tryptophan, 1 to 40 mg/l (preferably 2 to 30 mg/l); L-tyrosine disodium dihydrate, 2 to 300 mg/l (preferably 4 to 200 mg/l); and L-valine, 5 to 300 mg/l (preferably 10 to 200 mg/l).

The vitamins are added, for example, to give the following concentrations: d-biotin, 0.001 to 0.4 mg/l (preferably 0.002 to 0.3 mg/l); calcium D-pantothenate, 0.001 to 10.0 mg/l (preferably 0.002 to 7.5 mg/l); choline chloride, 0.1 to 20.0 mg/l (preferably 0.2 to 15.0 mg/l); folic acid, 0.005 to 20.0 mg/l (preferably 0.01 to 15.0 mg/l); myo-inositol, 0.01 to 300 mg/l (preferably 0.05 to 200 mg/l); niacinamide, 0.01 to 20.0 mg/l (preferably 0.02 to 15.0 mg/l); pyridoxal monohydrochloride, 0.01 to 15.0 mg/l (preferably 0.02 to 10.0 mg/l); riboflavin, 0.005 to 2.0 mg/l (preferably 0.01 to 1.5 mg/l); thiamine monohydrochloride, 0.005 to 20.0 mg/l (preferably 0.01 to 15.0 mg/l); and cyanocobalamin, 0.001 to 5.0 mg/l (preferably 0.002 to 3.0 mg/l).

The physiologically active substances are added, for example, to give the following concentrations: insulin, 10 to 500 mg/l, preferably 50 to 300 mg/l; transferrin, 10 to 500 mg/l, preferably 50 to 300 mg/l; and albumin, 200 to 6000 mg/l, preferably 700 to 4000 mg/l.

The batch culture is usually carried out at pH 6 to 8 at 30 to 40° C. for 3 to 12 days. If necessary, antibiotics such as streptomycin and penicillin may be added to the medium during the culturing. Further, control of dissolved oxygen concentration, pH control, temperature control, stirring and the like can be carried out according to general methods employed in the culturing of animal cells.

2. Fed-Batch Culture

The serum-free medium used in the process of the present invention is a medium prepared by adding, instead of serum, various physiologically active substances and nutrient factors, as well as carbon sources, nitrogen sources, etc. which can be assimilated by animal cells, to an ordinary basal medium employed for the culturing of animal cells.

Examples of suitable media include RPMI1640 medium [The Journal of the American Medical Association, 199, 519 (1967)], Eagle's MEM [Science, 122, 501 (1952)], Dulbecco's modified MEM [Virology, 8, 396 (1959)], 199 medium [Proceeding of the Society for the Biological Medicine, 73, 1 (1950)], F12 medium [Proc. Natl. Acad. Sci. USA, 53, 288 (1965)] and IMDM [J. Experimental Medicine, 147, 923 (1978)]. Preferred are DMEM, F12 medium and IMDM. In addition to the above media, the serum-free media described in the above description of batch culture are also useful.

To the serum-free medium are added physiologically active substances, nutrient factors, etc. required for the growth of animal cells according to need. These additives may be contained in the medium prior to the culturing or may be appropriately added to the culture during the culturing according to need.

The nutrient factors include glucose, amino acids and vitamins.

Examples of the amino acids are L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine, which may be used alone or in combination.

Examples of the vitamins are d-biotin, D-pantothenic acid, choline, folic acid, myo-inositol, niacinamide, pyridoxal, riboflavin, thiamine, cyanocobalamin and DL-α-tocopherol, which may be used alone or in combination.

The physiologically active substances include insulin, transferrin and albumin.

As for the final concentrations of the nutrient factors in the medium or culture, glucose is added to give a final concentration of 200 to 6000 mg/l, preferably 1000 to 5000 mg/l.

The amino acids are added, for example, to give the following final concentrations: L-alanine, 1 to 960 mg/l (preferably 1 to 640 mg/l); L-arginine monohydrochloride, 10 to 6000 mg/l (preferably 11 to 4000 mg/l); L-asparagine monohydrate, 10 to 1200 mg/l (preferably 11 to 800 mg/l); L-aspartic acid, 5 to 600 mg/l (preferably 5 to 400 mg/l); L-cystine dihydrochloride, 10 to 1200 mg/l (preferably 11 to 800 mg/l); L-glutamic acid, 5 to 1200 mg/l (preferably 5 to 800 mg/l); L-glutamine, 53 to 12000 (preferably 55 to 8000 mg/l); glycine, 2 to 600 mg/l (preferably 2 to 400 mg/l); L-histidine monohydrochloride dihydrate, 5 to 1200 mg/l (preferably 5 to 800 mg/l); L-isoleucine, 4 to 1800 mg/l (preferably 4 to 1200 mg/l); L-leucine, 13 to 1800 mg/l (preferably 14 to 1200 mg/l); L-lysine monohydrochloride, 10 to 1800 mg/l (preferably 11 to 1200 mg/l); L-methionine, 4 to 600 mg/l (preferably 5 to 400 mg/l); L-phenylalanine, 5 to 1200 mg/l (preferably 5 to 800 mg/l); L-proline, 5 to 1200 mg/l (preferably 5 to 800 mg/l); L-serine, 5 to 1200 mg/l (preferably 5 to 800 mg/l); L-threonine, 5 to 1200 mg/l (preferably 5 to 800 mg/l); L-tryptophan, 1 to 240 mg/l (preferably 1 to 160 mg/l); L-tyrosine disodium dihydrate, 8 to 1800 mg/l (preferably 8 to 1200 mg/l); and L-valine, 12 to 1800 mg/l (preferably 12 to 1200 mg/l).

The vitamins are added, for example, to give the following final concentrations: d-biotin, 0.001 to 2.4 mg/l (preferably 0.001 to 1.6 mg/l); calcium D-pantothenate, 0.011 to 60 mg/l (preferably 0.011 to 40 mg/l); choline chloride, 0.11 to 90 mg/l (preferably 0.11 to 60 mg/l); folic acid, 0.01 to 120 mg/l (preferably 0.01 to 80 mg/l); myo-inositol, 0.05 to 1800 mg/l (preferably 0.05 to 1200 mg/l); niacinamide, 0.02 to 120 mg/l (preferably 0.03 to 80 mg/l); pyridoxal monohydrochloride, 0.02 to 90 mg/l (preferably 0.03 to 60 mg/l); riboflavin, 0.01 to 12 mg/l (preferably 0.01 to 9.8 mg/l); thiamine monohydrochloride, 0.01 to 120 mg/l (preferably 0.01 to 80 mg/l); and cyanocobalamin, 0.001 to 30 mg/l (preferably 0.001 to 20 mg/l).

The physiologically active substances are added to the medium or culture, for example, to give the following final concentrations: insulin, 10 to 3000 mg/l, preferably 11 to 2000 mg/l; transferrin, 10 to 3000 mg/l, preferably 11 to 2000 mg/l; and albumin, 200 to 36000 mg/l, preferably 220 to 24000 mg/l.

In the present invention, the "final concentration" of a substance is expressed as the value obtained by dividing, after the final addition of concentrated culture medium during the fed-batch culture, the total weight of the substance contained in the medium and that added to the culture by the total volume of the medium and the concentrated culture medium added.

In the fed-batch culture, it is preferred to add the physiologically active substances, nutrient factors, etc. at higher concentrations than usually employed. For example, they are added in an amount of 1/30 to 1/3, preferably 1/20 to 1/5 the volume of culture at a time. In the case of addition to the culture, they are preferably added continuously or in several to over ten portions during the culturing. According to the above-described fed-batch culture which comprises adding the physiologically active substances, nutrient factors, etc. continuously or intermittently in small portions, a high metabolic efficiency of cells can be attained and the lowering of the finally attained density of cultured cells due to the accumulation of waste matters in the culture can be prevented. Further, the concentration of the desired polypeptide in the recovered culture is higher than that in the batch culture, which facilitates the separation and purification of the polypeptide and thus improves the productivity of the polypeptide per medium compared with the batch culture.

The fed-batch culture is usually carried out at pH 6 to 8 at 30 to 40° C. for 3 to 12 days. If necessary, antibiotics such as streptomycin and penicillin may be added to the medium during the culturing. Further, control of dissolved oxygen concentration, pH control, temperature control, stirring and the like can be carried out according to general methods employed in the culturing of animal cells.

3. Perfusion Culture

The serum-free medium used in the process of the present invention is a medium prepared by adding, instead of serum, various physiologically active substances and nutrient factors, as well as carbon sources, nitrogen sources, etc. which can be assimilated by animal cells, to an ordinary basal medium employed for the culturing of animal cells.

Examples of suitable media include RPMI1640 medium [The Journal of the American Medical Association, 199, 519 (1967)], Eagle's MEM [Science, 122, 501 (1952)], Dulbecco's modified MEM [Virology, 8, 396 (1959)], 199 medium [Proceeding of the Society for the Biological Medicine, 73, 1 (1950)], F12 medium [Proc. Natl. Acad. Sci. USA, 53, 288 (1965)] and IMDM [J. Experimental Medicine, 147, 923 (1978)]. Preferred are DMEM, F12 medium and IMDM. In addition to the above media, the serum-free media described in the above description of batch culture are also useful.

To the serum-free medium are added physiologically active substances, nutrient factors, etc. required for the growth of animal cells according to need. These additives are preferably added to the medium prior to the culturing or to the medium to be supplied to the culture.

The nutrient factors include glucose, amino acids and vitamins.

Examples of the amino acids are L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine, which may be used alone or in combination.

Examples of the vitamins are d-biotin, D-pantothenic acid, choline, folic acid, myo-inositol, niacinamide, pyridoxal, riboflavin, thiamine, cyanocobalamin and DL-α-tocopherol, which may be used alone or in combination.

The physiologically active substances include insulin, transferrin and albumin.

As for the concentrations of the nutrient factors, the concentration of glucose is controlled at 500 to 6000 mg/l, preferably 1000 to 2000 mg/l.

The nutrient factors include amino acids and vitamins. The other physiologically active substances or nutrient factors are added, for example, to give the following concentrations: insulin, 4 to 560 mg/l, preferably 20 to 360 mg/l; transferrin, 4 to 560 mg/l, preferably 20 to 360 mg/l; and albumin, 80 to 6500 mg/l, preferably 280 to 4500 mg/l.

Examples of the amino acids are L-alanine, L-arginine, L-asparagine, L-aspartic acid, L-cystine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine, which may be used alone or in combination. The amino acids are added, for example, to give the following concentrations: L-alanine, 1 to 200 mg/l (preferably 2 to 160 mg/l); L-arginine monohydrochloride, 10 to 1140 mg/l (preferably 30 to 940 mg/l); L-asparagine monohydrate, 10 to 250 mg/l (preferably 20 to 200 mg/l); L-aspartic acid, 5 to 148 mg/l (preferably 10 to 120 mg/l); L-cystine dihydrochloride, 10 to 350 mg/l (preferably 20 to 300 mg/l); L-glutamic acid, 5 to 320 mg/l (preferably 10 to 270 mg/l); L-glutamine, 50 to 3300 (preferably 100 to 1800 mg/l); glycine, 2 to 148 mg/l (preferably 5 to 123 mg/l); L-histidine monohydrochloride dihydrate, 5 to 270 mg/l (preferably 10 to 220 mg/l); L-isoleucine, 4 to 470 mg/l (preferably 4 to 370 mg/l); L-leucine, 10 to 470 mg/l (preferably 13 to 370 mg/l); L-lysine monohydrochloride, 10 to 530 mg/l (preferably 20 to 480 mg/l); L-methionine, 4 to 150 mg/l (preferably 4 to 120 mg/l); L-phenylalanine, 4 to 310 mg/l (preferably 4 to 260 mg/l); L-proline, 5 to 270 mg/l (preferably 10 to 210 mg/l); L-serine, 5 to 270 mg/l (preferably 10 to 220 mg/l); L-threonine, 5 to 350 mg/l (preferably 10 to 300 mg/l); L-tryptophan, 1 to 65 mg/l (preferably 2 to 55 mg/l); L-tyrosine disodium dihydrate, 4 to 470 mg/l (preferably 8 to 370 mg/l); and L-valine, 10 to 450 mg/l (preferably 11 to 350 mg/l).

Examples of the vitamins are d-biotin, D-pantothenic acid, choline, folic acid, myo-inositol, niacinamide, pyridoxal, riboflavin, thiamine, cyanocobalamin and DL-α-tocopherol, which may be used alone or in combination. The vitamins are added, for example, to give the following final concentrations: d-biotin, 0.001 to 0.44 mg/l (preferably 0.02 to 0.34 mg/l); calcium D-pantothenate, 0.01 to 16 mg/l (preferably 0.02 to 14 mg/l); choline chloride, 0.1 to 21 mg/l (preferably 0.2 to 16 mg/l); folic acid, 0.01 to 26 mg/l (preferably 0.01 to 21 mg/l); myo-inositol, 0.05 to 310 mg/l (preferably 0.05 to 211 mg/l); niacinamide, 0.02 to 26 mg/l (preferably 0.02 to 21 mg/l); pyridoxal monohydrochloride, 0.02 to 21 mg/l (preferably 0.02 to 16 mg/l); riboflavin, 0.01 to 2.6 mg/l (preferably 0.01 to 2.1 mg/l); thiamine monohydrochloride, 0.01 to 26 mg/l (preferably 0.01 to 21 mg/l); and cyanocobalamin, 0.001 to 5 mg/l (preferably 0.002 to 3 mg/l).

In accordance with the present invention, the culture is efficiently separated by use of an apparatus usually employed for separating cells from a culture. The concentrated culture containing the cells is returned to the incubator and a fresh medium is added for supplement the reduced culture, whereby desirable culturing conditions can be maintained during the culturing process.

The productivity of the desired polypeptide by the cells of the present invention can be enhanced by stabilizing the culturing system by discarding the proliferated cells from the system according to the cell growth rate, apart from the rate of replacement with a fresh medium. For instance, it is possible to carry out culturing with a high productivity by discarding the cells from the system at a rate in accordance with the cell growth rate, i.e., discarding ⅖ to ⅗ of all the cells existing in the incubator during the doubling time so that the desired cell density can be maintained.

The culturing according to the present invention is usually carried out at pH 6 to 8 at 30 to 40° C. for 10 to 40 days. If necessary, antibiotics such as streptomycin and penicillin may be added to the medium during the culturing. Further, control of dissolved oxygen concentration, pH control, temperature control, stirring and the like can be carried out according to general methods employed in the culturing of animal cells.

As described above, the desired polypeptide can be produced by culturing the rat cells of the present invention, allowing the polypeptide to form and accumulate, and recovering the polypeptide from the culture.

In the present invention, it is preferred to carry out the culturing with the insulin concentration in the culture kept at 10 mg/l or above, preferably 20 mg/l or above in order to grow the cells. On the other hand, in order to produce the desired polypeptide, it is preferred to carry out the culturing with the insulin concentration in the culture kept at 10 mg/l or below, preferably 5 mg/l or below. When the medium for the former culturing contains insulin, it is not necessary to add insulin in order to enhance the productivity of antibody. However, the insulin concentration in the culture is usually kept at 0.01 to 10 mg/l, preferably 0.01 to 5 mg/l.

The methods of adjusting the insulin concentration in the culture are advantageously employed in the culturing capable of insulin concentration adjustment, e.g., fed-batch culture and perfusion culture.

In the present invention, the desired polypeptide may be produced by the direct expression method in which the polypeptide is produced in the host cells or by the method in which the polypeptide is secreted outside the host cells (Molecular Cloning, 2nd ed.).

It is possible to have the desired polypeptide actively secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc. That is, the desired polypeptide can be actively secreted outside the host cells by expressing it in the form of a polypeptide in which a signal peptide is added upstream of the polypeptide of the present invention by the use of recombinant DNA techniques.

It is also possible to increase the production of the desired polypeptide by utilizing a gene amplification system using a dihydrofolate reductase gene or the like according to the method described in Japanese Published Unexamined Patent Application No. 227075/90.

The desired polypeptide produced by the process of the present invention can be isolated and purified by general methods for isolating and purifying polypeptides.

When the polypeptide produced by the process of the present invention is intracellularly expressed in a soluble form, the cells are recovered by centrifugation after the completion of culturing and suspended in an aqueous buffer, followed by disruption using sonicator, French press, Manton-Gaulin homogenizer, Dynomill or the like to obtain a cell-free extract. From the supernatant obtained by centrifuging the cell-free extract, a purified polypeptide preparation can be obtained by using general methods for isolating and purifying enzymes, i.e., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Kasei Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography using protein A, chromatofocusing, electrophoresis such as isoelectric focusing, etc., singly or in combination.

When the polypeptide produced by the process of the present invention is secreted extracellularly, the polypeptide can be recovered in the culture supernatant. That is, the culture is treated by the same means as above, e.g., centrifugation, to obtain the culture supernatant. From the culture supernatant, a purified polypeptide preparation can be obtained by using the same isolation and purification methods as above.

Among the polypeptides produced by the process of the present invention, immunologically functional molecules, especially antibodies, have a high antibody-dependent cell-mediated cytotoxic activity (ADCC activity) and are useful for the treatment of diseases such as tumor, inflammation and allergy.

BEST MODES FOR CARRYING OUT THE INVENTION

Figure 1:
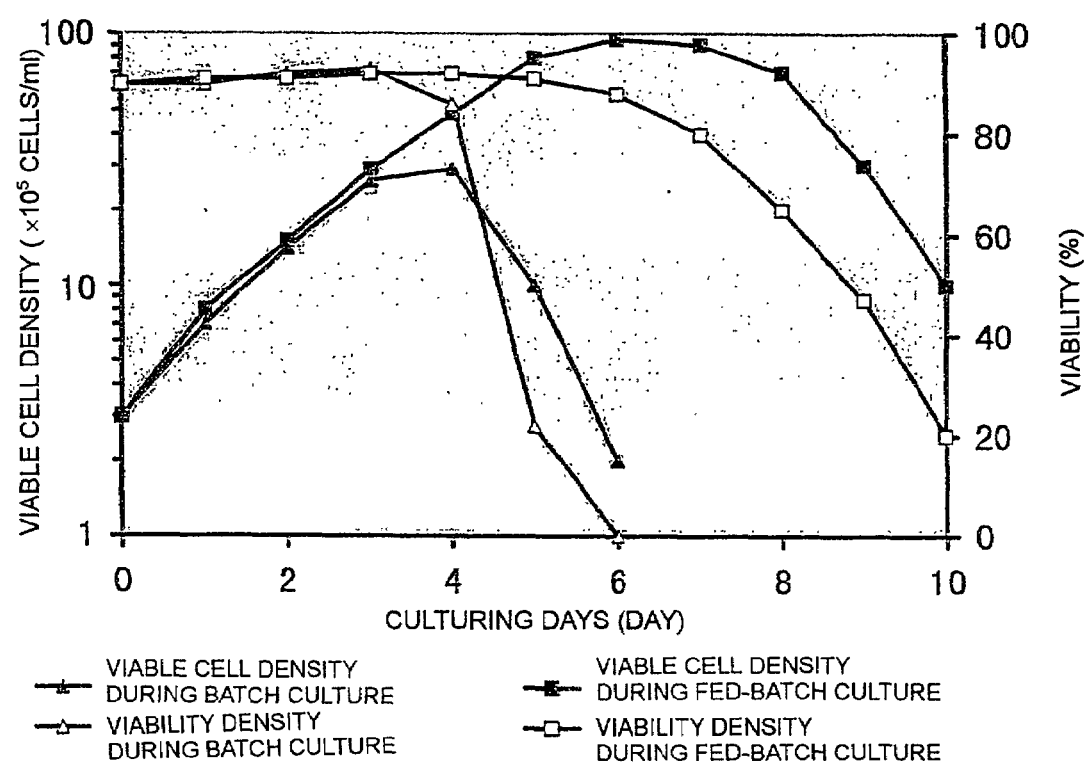
FIG. 1 shows the change in viable cell density and viability during the culturing of anti-GD3 chimeric antibody-producing cell line 61-33γ (FERM BP-7325) adapted to a serum-free medium.

Examples of the present invention are shown below.

Example 1

Production of Anti-GD3 Chimeric Antibody

1. Construction of Tandem Expression Vector pChiLHGM4 for Anti-GD3 Human Chimeric Antibody The expression vector pChi641LGM4 for L-chain of anti-GD3 chimeric antibody [J. Immunol. Methods, 167, 271 (1994)] was cleaved with restriction enzymes MluI (Takara Shuzo Co., Ltd.) and SalI (Takara Shuzo Co., Ltd.) to obtain a fragment of ca. 4.03 kb comprising the L-chain cDNA. Separately, the expression vector pAGE107 for animal cells [Cytotechnology, 3, 133 (1990)] was cleaved with restriction enzymes MluI (Takara Shuzo Co., Ltd.) and SalI (Takara Shuzo Co., Ltd.) to obtain a fragment of ca. 3.40 kb comprising the G418 resistance gene and the splicing signal. The obtained fragments were ligated using DNA Ligation Kit (Takara Shuzo Co., Ltd.) and *Escherichia coli* HB101 (Molecular Cloning: A Laboratory Manual, Cold Spring Harbor Lab. Press, New York, 1989) was transformed with the ligation product to construct plasmid pChi641LGM40.

The plasmid pChi641LGM40 constructed above was cleaved with restriction enzyme ClaI (Takara Shuzo Co., Ltd.) and blunted using DNA Blunting Kit (Takara Shuzo Co., Ltd.), followed by cleavage with MluI (Takara Shuzo Co., Ltd.) to obtain a fragment of ca. 5.68 kb comprising the L-chain cDNA. Separately, the expression vector pChi641HGM4 for H-chain of anti-GD3 chimeric antibody [J. Immunol. Methods, 167, 271 (1994)] was cleaved with restriction enzyme XhoI (Takara Shuzo Co., Ltd.) and blunted using DNA Blunting Kit (Takara Shuzo Co., Ltd.), followed by cleavage with MluI (Takara Shuzo Co., Ltd.) to obtain a fragment of ca. 8.40 kb comprising the H-chain cDNA. The thus obtained fragments were ligated using DNA Ligation Kit (Takara Shuzo Co., Ltd.) and *Escherichia coli* HB101 (Molecular Cloning: A Laboratory Manual, Cold Spring Harbor Lab. Press, New York, 1989) was transformed with the ligation product to construct tandem expression vector pChi641LHGM4 for anti-GD3 chimeric antibody.

2. Preparation of a Producing Cell Using Rat Myeloma Cell YB2/0

The tandem expression vector pChi641LHGM4 for anti-GD3 chimeric antibody constructed in Example 1-1 (5 μg) was introduced into YB2/0 rat myeloma cells ($4 \times 10^6$ cells/ml) by electroporation [Cytotechnology, 3, 133 (1990)], and the resulting cells were suspended in 40 ml of RPMI1640-FBS (10) [RPMI1640 medium containing 10% FBS (GIBCO BRL)] and put into wells of a 96-well culture plate (Sumitomo Bakelite Co., Ltd.) in an amount of 200 μl/well. After culturing in a 5% $CO_2$ incubator at 37° C. for 24 hours, G418 was added to give a concentration of 0.5 mg/ml, followed by further culturing for 1 to 2 weeks. The culture supernatants were collected from the wells in which a colony of transformant exhibiting G418-resistance appeared and growth was observed, and the antigen-binding activity of anti-GD3 chimeric antibodies in the supernatants was measured by ELISA as described in Example 1-3.

The transformants in the wells containing culture supernatants in which the production of anti-GD3 chimeric antibody was observed were treated in the following manner in order to increase the antibody production by utilizing the DHFR gene amplification system. That is, the transformant cells were suspended in RPMI1640-FBS(10) containing 0.5 mg/ml G418 and 50 nM methotrexate (a DHFR inhibitor; hereinafter referred to as MTX; Sigma Chemical Co.) at a density of 1 to $2 \times 10^5$ cells/ml and put into wells of a 24-well plate (Greiner) in an amount of 2 ml per well. Culturing was carried out in a 5% $CO_2$ incubator at 37° C. for 1 to 2 weeks to obtain transformants exhibiting the resistance to 50 nM MTX.

The antigen-binding activity of anti-GD3 chimeric antibodies in the culture supernatants in the wells in which the growth of transformant was observed was measured by ELISA as described in Example 1-3. The transformants in the wells containing culture supernatants in which the production of anti-GD3 chimeric antibody was observed were treated in a manner similar to the above with the MTX concentration successively raised (100 nM and 200 nM) to finally obtain transformants which are capable of growing in RPMI1640-FBS(10) containing 0.5 mg/ml G418 and 200 nM MTX and which highly produce anti-GD3 chimeric antibodies. The obtained transformants were cloned by carrying out limiting dilution twice.

The thus obtained anti-GD3 chimeric antibody-producing transformant clone 7-9-51 was deposited with the National Institute of Bioscience and Human-Technology, Agency of Industrial Science and Technology, 1-3, Higashi 1-chome, Tsukuba-shi, Ibaraki, Japan, on Apr. 5, 1999 as FERM BP-6691.

3. Measurement of GD3-Binding Activity of Antibodies (ELISA)

The GD3-binding activity of antibodies was measured in the following manner.

GD3 (4 nmol) was dissolved in 2 ml of ethanol containing 10 μg of dipalmitoyl phosphatidylcholine (Sigma Chemical Co.) and 5 μg of cholesterol (Sigma Chimical Co.), and 20 μl portions of the solution (40 pmol/well) were put into wells of a 96-well plate for ELISA (Greiner). After air-drying, PBS containing 1% bovine serum albumin (Sigma Chemical Co.; hereinafter referred to as BSA) (this PBS is hereinafter referred to as 1% BSA-PBS) was added to the wells in an amount of 100 μl/well, followed by reaction at room temperature for one hour to block the remaining active groups. Then, the 1% BSA-PBS was discarded, and 50 μl each of the culture supernatant of transformant or variously diluted solutions of a purified human chimeric antibody was respectively added to the wells, followed by reaction at room temperature for one hour. After the reaction, the wells were washed with PBS containing 0.05% Tween 20 (Wako Pure Chemical Industries, Ltd.) (hereinafter referred to as Tween-PBS). To each well was added 50 μl of peroxidase-labeled goat anti-human IgG (H & L) antibody solution (American Qualex) diluted 3000-fold with 1% BSA-PBS as a secondary antibody solution, followed by reaction at room temperature for one hour. After the reaction, the wells were washed with Tween-PBS, and 50 μl of ABTS substrate solution [a solution prepared by dissolving 0.55 g of 2,2'-azino-bis(3-ethylbenzothiazoline-6-sulfonic acid) ammonium in 1 l of 0.1 M citrate buffer (pH 4.2) and adding thereto, just before use, 1 μl/ml hydrogen peroxide] was added to each well to develop color. Then, the absorbance at 415 nm (hereinafter referred to as OD 415) was measured.

Example 2

The anti-GD3 antibody-producing transformant clone 7-9-51 (FERM BP-6691) was adapted to a serum-free medium in the following manner. In all steps, culturing was carried out by static subculture in a T flask under the following conditions: temperature, 37° C.; $CO_2$ concentration, 5%; amount of culture, 5 ml. When the cells were passaged, the whole culture liquor was replaced with a fresh medium by centrifugation.

FERM BP-6691 was inoculated into a serum-containing medium prepared by adding bovine serum albumin (BSA; JRH), insulin (Life Technologies, Inc.) and transferrin (Life Technologies, Inc.) to a basal medium for adaptation to serum-free conditions comprising IMD medium (Life Technologies, Inc.) and 200 nM MTX (Sigma Chemical Co.) at a cell density of 2 to $4 \times 10^5$ cells/ml, and subcultured (period for one passage: 2 to 4 days).

The cells obtained by the above subculturing were subcultured in a serum-containing medium prepared by adding 5% (v/v) γ-ray-irradiated dialyzed fetal bovine serum (dFBS; Life Technologies, Inc.) and 100 nM T3 to the above basal medium. Then, subculturing of the cells was serially carried out using the following media: a medium prepared by adding 0.2% (W/v) BSA, 50 mg/l insulin and 50 mg/l transferrin to the above basal medium (9 passages, 27 days); a medium prepared by adding 0.2% (w/v) BSA, 20 mg/l insulin and 20 mg/l transferrin to the above basal medium (one passage, 3 days); a medium prepared by adding 0.1% (w/v) BSA, 20 mg/l insulin and 20 mg/l transferrin to the above basal medium (one passage, 3 days); and a medium prepared by adding 0.05% (w/v) BSA, 10 mg/l insulin and 10 mg/l transferrin to the above basal medium (one passage, 3 days).

In preparing a cell line adapted to a serum-free medium, the viability of cells lowered intermittently during the culturing for 27 days in the medium prepared by adding 0.2% (w/v) BSA, 50 mg/l insulin and 50 mg/l transferrin to the above basal medium. As a result of attempts to solve this problem, the cells could be adapted to a serum-free medium without lowering of the viability of cells by inoculating the cells into the medium at a density of $4 \times 10^5$ cells/ml.

Cloning of the rat cells adapted to a serum-free medium was carried out by limiting dilution in the following manner.

A cell suspension was prepared and put into wells of 96-well plates in an amount of 0.25 cell/well and 0.2 ml/well. The cells were seeded in 1632 wells in total, and as a result, 72 clones were obtained. The procedure was repeated on a larger scale using 6-well plates and then Erlenmeyer flasks, and 3 clones were selected based on the productivity and growth. Among these, one having a high productivity was designated 61-33γ cell line. The cell line 61-33γ adapted to a serum-free medium was deposited with the National Institute of Bioscience and Human-Technology, Agency of Industrial Science and Technology, 1-3, Higashi 1-chome, Tsukuba-shi, Ibaraki, Japan, on Oct. 13, 2000 as FERM BP-7325.

The thus obtained cell line 61-33γ adapted to a serum-free medium could be stably subcultured for a period of 110 days by carrying out subculturing in a medium prepared by adding 0.2% (w/v) BSA, 10 mg/l insulin, 10 mg/l transferrin and 200 nM MTX to the above serum-free basal medium (period for one passage: 3 to 5 days).

FERM BP-7325 was inoculated into a serum-free medium prepared by adding 0.1% (w/v) BSA and 200 nM MTX to Hybridoma-SFM at a density of $3 \times 10^6$ cells/ml, and subjected to batch culture in a 5% $CO_2$ incubator at 37° C. for 3 days. At the completion of culturing, the cell density was $17.5 \times 10^6$ cells/ml and the antibody concentration in the supernatant was 39 mg/l.

On the other hand, FERM BP-6691 was inoculated into a serum-containing medium prepared by adding 10% (v/v) dFBS and 200 nM MTX to IMD medium at a density of $3 \times 10^6$ cells/ml, and subjected to batch culture in a 5% $CO_2$ incubator at 37° C. for 3 days. At the completion of culturing, the cell density was $14.2 \times 10^6$ cells/ml and the antibody concentration in the supernatant was 28 mg/l.

Example 3

Batch culture of FERM BP-7325 was carried out using a spinner flask containing a serum-free medium.

FERM BP-7325 was subjected to static culture using a T-225-cm$^2$ flask containing 30 ml of a serum-free medium (Hybridoma-SFM; Life Technologies, Inc.) in a 5% $CO_2$ incubator at 37° C. for 3 days. The resulting FERM BP-7325 was inoculated into 0.7 l of a serum-free medium (Hybridoma-SFM; Life Technologies, Inc.) in a 1-l spinner flask (Shibata Hario Co., Ltd.) at a density of $3 \times 10^5$ cells/ml.

Culturing was carried out with stirring at 30 rpm while the pH of culture was controlled at 7.1±0.1 and the dissolved oxygen concentration was controlled at 5±0.2 ppm. Aeration was carried out by supplying a mixed gas of air, oxygen and carbon dioxide through a porous Teflon tube installed in the spinner flask. The pH was controlled by changing the ratio between air and carbon dioxide, and by supplying 1 M sodium carbonate solution. The dissolved oxygen concentration was controlled by changing the ratio between air and oxygen.

Figure 2:
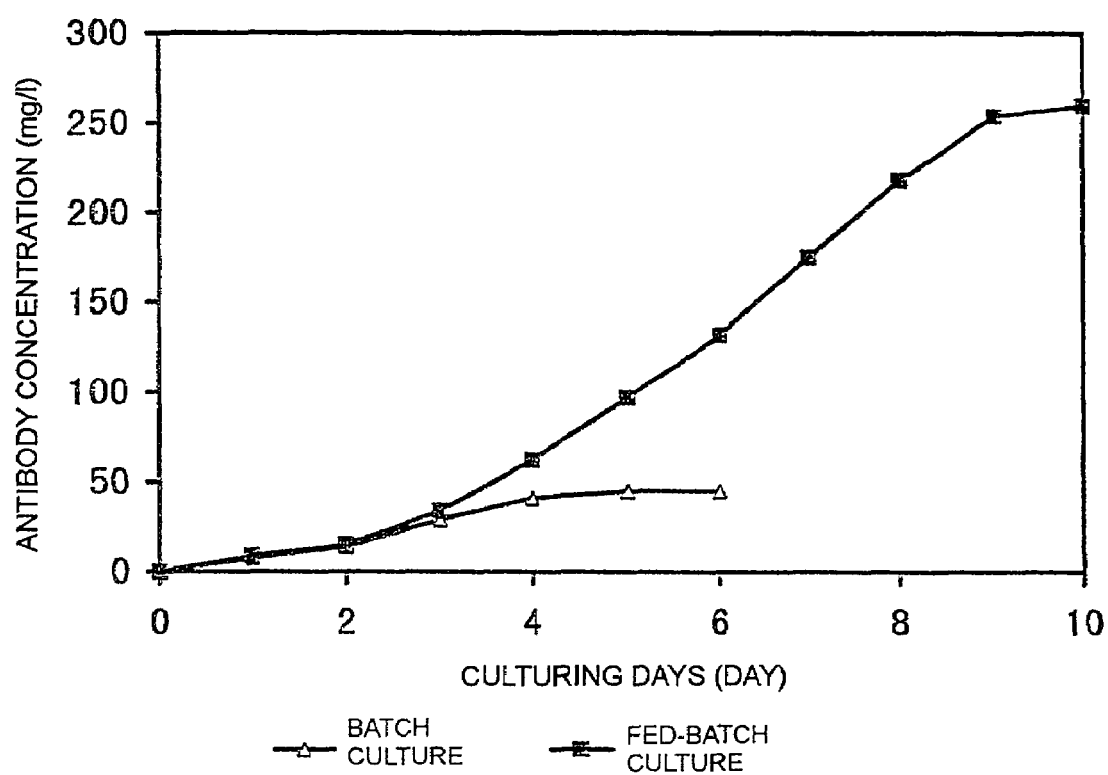
FIG. 2 shows the change in antibody concentration of anti-GD3 chimeric antibody KM-871 during the culturing of anti-GD3 chimeric antibody-producing cell line 61-33γ (FERM BP-7325) adapted to a serum-free medium.

The results are shown in FIG. 1 and FIG. 2.

As shown in FIG. 1 and FIG. 2, the cells showed logarithmic growth until the 3rd day of culturing, but thereafter the specific growth rate lowered. The viable cell density reached a maximum of ca. $3 \times 10^6$ cells/ml on the 4th day, and then rapidly lowered. On the 6th day of culturing, the viability lowered to less than 10%, and the culturing was finished.

The antibody production by culturing for 6 days was 45 mg/l and thus the antibody production rate by batch culture was 7.5 mg/l/day.

Example 4

Fed-batch culture of FERM BP-7325 was carried out using a spinner flask containing a serum-free medium.

FERM BP-7325 was subjected to static culture using a T-225-cm² flask containing 30 ml of a serum-free medium (Hybridoma-SFM; Life Technologies, Inc.) in a 5% $CO_2$ incubator at 37° C. for 3 days. The resulting FERM BP-7325 was inoculated into 0.7 l of Hybridoma-SFM in a 1-l spinner flask (Shibata Hario Co., Ltd.) at a density of $3 \times 10^5$ cells/ml.

For the purpose of compensating the consumption of amino acids estimated from the specific consumption rate thereof, a feed medium comprising amino acids (0.140 g/l L-alanine, 0.470 g/l L-arginine monohydrochloride, 0.159 g/l L-asparagine monohydrate, 0.168 g/l L-aspartic acid, 0.511 g/l L-cystine dihydrochloride, 0.420 g/l L-glutamic acid, 4.677 g/l L-glutamine, 0.168 g/l glycine, 0.235 g/l L-histidine monohydrochloride dihydrate, 0.588 g/l L-isoleucine, 0.588 g/l L-leucine, 0.818 g/l L-lysine monohydrochloride, 0.168 g/l L-methionine, 0.370 g/l L-phenylalanine, 0.224 g/l L-proline, 0.235 g/l L-serine, 0.532 g/l L-threonine, 0.090 g/l L-tryptophan, 0.581 g/l L-tyrosine disodium dihydrate, and 0.526 g/l L-valine), vitamins (0.0728 mg/l d-biotin, 0.0224 g/l calcium D-pantothenate, 0.0224 g/l choline chloride, 0.0224 g/l folic acid, 0.0403 g/l myo-inositol, 0.0224 g/l niacinamide, 0.0224 g/l pyridoxal hydrochloride, 0.00224 g/l riboflavin, 0.0224 g/l thiamine hydrochloride, and 0.0728 mg/l cyanocobalamin), 0.2 g/l insulin, 0.2 g/l transferrin, and 1.6 g/l albumin, which were adjusted to higher concentrations than usual concentrations for addition, was added in 0.07-l portions once a day or with less frequency when the cumulative viable cell density exceeded $4 \times 10^6$ cells/ml×day. In other words, 0.07 l of the feed medium was added on the 3rd, 5th, 6th, 7th and 8th days of culturing. On the 3rd day of culturing and thereafter, 100 g/l glucose solution was added at appropriate times so that the glucose concentration in the culture immediately after addition would be ca. 2500 mg/l.

Culturing was carried out with stirring at 30 rpm while the pH of culture was controlled at 7.1±0.1 and the dissolved oxygen concentration was controlled at 5±0.2 ppm. Aeration was carried out by supplying a mixed gas of air, oxygen and carbon dioxide through a porous Teflon tube installed in the spinner flask. The pH was controlled by changing the ratio between air and carbon dioxide, and by supplying 1 M sodium carbonate solution. The dissolved oxygen concentration was controlled by changing the ratio between air and oxygen.

The results are shown in FIG. 1 and FIG. 2.

The cells showed logarithmic growth until the 5th day of culturing. Though the specific growth rate lowered on and after the 5th day of culturing, the viable cell density reached ca. $1 \times 10^7$ cells/ml on the 6th day of culturing.

After the viable cell density reached a maximum, the viable cell density and viability lowered slowly. On the 10th day of culturing, the viability lowered to less than 20%, and the culturing was finished.

The antibody production by culturing for 10 days was 260 mg/l and thus the antibody production rate by fed-batch culture was 26.0 mg/l/day, which means that the antibody production rate improved as compared with that by batch culture on the same scale, i.e. about 3.5 times that by batch culture.

Example 5

Continuous culture of FERM BP-7325 was carried out using a spinner flask containing a serum-free medium. In order to carry out perfusion in the continuous culture, solid-liquid separation of concentrated culture containing the cells and culture supernatant was conducted by using a centrifuge.

FERM BP-7325 was subjected to static culture using a T-225-cm² flask containing 30 ml of a serum-free medium (Hybridoma-SFM; Life Technologies, Inc.) in a 5% $CO_2$ incubator at 37° C. for 3 days. The resulting FERM BP-7325 was inoculated into 1 l of a medium prepared by adding 18% (v/v) supplementation medium comprising amino acids (0.220 g/l L-alanine, 0.739 g/l L-arginine monohydrochloride, 0.264 g/l L-asparagine monohydrate, 0.220 g/l L-aspartic acid, 0.803 g/l L-cystine dihydrochloride, 0.660 g/l L-glutamic acid, 7.34 g/l L-glutamine, 0.264 g/l glycine, 0.370 g/l L-histidine monohydrochloride dihydrate, 0.924 g/l L-isoleucine, 0.924 g/l L-leucine, 1.285 g/l L-lysine monohydrochloride, 0.264 g/l L-methionine, 0.581 g/l L-phenylalanine, 0.352 g/l L-proline, 0.370 g/l L-serine, 0.836 g/l L-threonine, 0.141 g/l L-tryptophan, 0.915 g/l L-tyrosine disodium dihydrate, and 0.827 g/l L-valine), vitamins (0.114 mg/l d-biotin, 0.0352 g/l calcium D-pantothenate, 0.0352 g/l choline chloride, 0.0352 g/l folic acid, 0.0634 g/l myo-inositol, 0.0352 g/l niacinamide, 0.0352 g/l pyridoxal hydrochloride, 0.00352 g/l riboflavin, 0.0352 g/l thiamine hydrochloride, and 0.114 mg/l cyanocobalamin), 0.3 g/l insulin, 0.3 g/l transferrin, and 2.5 g/l albumin to Hybridoma-SFM in a 1-l spinner flask (Shibata Hario Co., Ltd.) at a density of $3 \times 10^5$ cells/ml.

Perfusion was started when the cell density reached $1 \times 10^6$ cells/ml. Then, the perfusion rate, i.e. the rate of medium replacement per day was raised according to the cell count, and when it was made 1 l/day, the viable cell density entered the maintenance phase. As an apparatus for solid-liquid separation, a small-sized continuous centrifuge for cell culture (Lab-II; Sobal) was used.

Culturing was carried out for 35 days, during which the small-sized continuous centrifuge for cell culture was operated at 800 rpm from the start of culturing till the viable cell density reached $1 \times 10^7$ cells/ml, and at 400 rpm (18×G) after the viable cell density reached $1 \times 10^7$ cells/ml.

When the rotation rate of the centrifuge was set at 800 rpm, almost all the cells were recovered within the system and only the culture supernatant containing few cells was discharged from the system. When the rotation rate of the centrifuge was set at 400 rpm, ½ of all the cells were discharged from the system, and thus the number of cells discharged from the system was counterbalanced by the number of cells increased by growth to keep the cell density constant.

Figure 3:
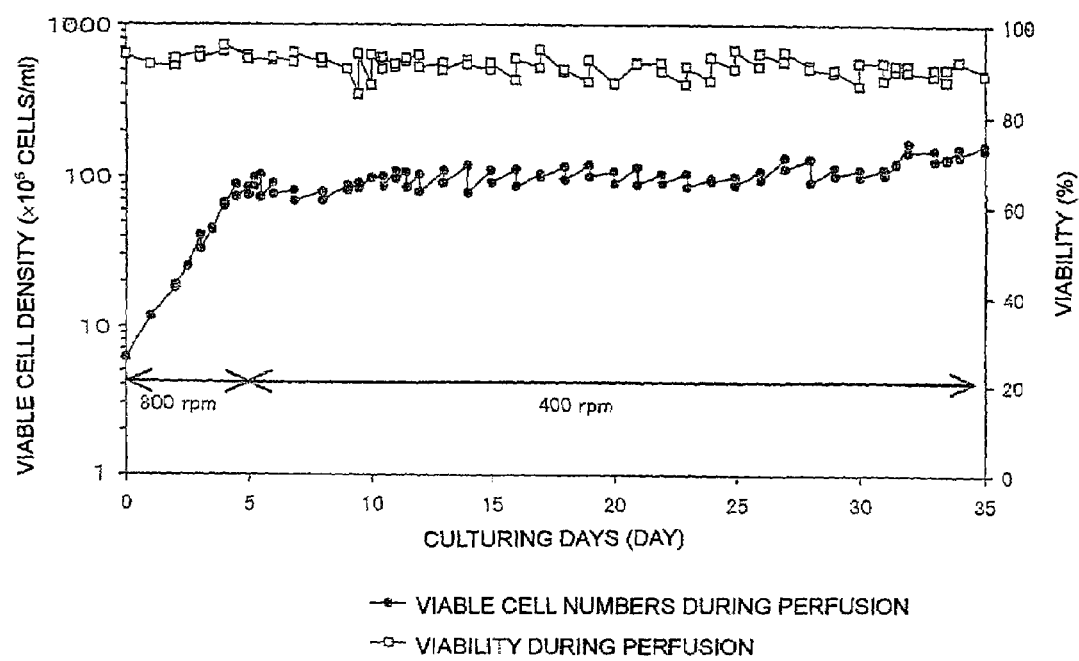
FIG. 3 shows the change in viable cell density and viability during the perfusion culture of anti-GD3 chimeric antibody-producing cell line 61-33γ (FERM BP-7325) adapted to a serum-free medium.

The viable cell density and viability of FERM BP-7325 during the perfusion culture are shown in FIG. 3.

As shown in FIG. 3, the viable cell density was maintained at $1 \times 10^7$ cells/ml for 30 days after the 5th day of culturing and the viability was maintained at 90% through the culturing period. The antibody production by culturing for 35 days was 2200 mg/l and thus the antibody production rate by perfusion culture was 62.9 mg/l/day.

Example 6

FERM BP-7325 was inoculated into a medium prepared by adding 20 mg/l insulin to Hybridoma-SFM (Life Technologies, Inc.) containing no insulin in a T-75 flask, and subcultured. After the completion of culturing, the culture was centrifuged to remove the supernatant and to recover the cells. The recovered cells were inoculated into Hybridoma-SFM containing no insulin in a T-75 static culture flask, and cultured for 3 days. After the completion of culturing, the culture was centrifuged to remove the supernatant and to recover the cells.

The recovered cells were suspended in media prepared by respectively adding 0, 5, 10 and 20 mg/l insulin to Hybridoma-SFM containing no insulin and inoculated into T-flasks, followed by static culture in a 5% $CO_2$ incubator at 37° C. for 6 days.

After the completion of culturing, the viable cell count and antibody concentration in each culture were measured, and the specific production rate of antibody was calculated.

The results are shown in Table 1.

TABLE 1

| Insulin concentration (mg/l) | Specific production rate ($\mu g/10^6$/day) |
| --- | --- |
| 0 | 13.1 |
| 5.0 | 9.0 |
| 10.0 | 7.6 |
| 20.0 | 7.8 |

As shown in Table 1, the highest productivity of antibody was obtained by use of the medium which was not supplemented with insulin, i.e. the medium containing insulin remaining in a trace amount, and the productivity was high also in the medium containing 5 mg/l insulin.

The cell growth rate lowered a little in an insulin concentration-dependent manner but a remarkable lowering was not observed.

INDUSTRIAL APPLICABILITY

The present invention provides a process for producing desired polypeptides using rat cells. Specifically, the antibodies obtained by the process of the present invention have high ADCC activity and are useful as pharmaceutical agents.

The invention claimed is:

1. A process for producing a polypeptide which comprises:
    (a) selecting a rat cell line capable of adapting in a serum-free medium
    (b) culturing the rat cell line selected in step (a) in a serum-free medium while an insulin concentration in the culture is maintained at 10 mg/l or above, followed by culturing while an insulin concentration in the culture is maintained at 20 mg/l or below, and
    (c) recovering the desired polypeptide from the culture,
    wherein the step (a) is carried out by inoculating a rat cell line into a serum-free medium at the cell density of $1 \times 10^5$ to $10 \times 10^5$ cells/ml of serum free medium and selecting a rat cell line that reaches a cell density of $10 \times 10^5$ to $40 \times 10^5$ cells/ml of serum-free medium.

2. The process according to claim 1, wherein the rat cell line adapted to a serum-free medium is a rat cell line which can be subcultured in a serum-free medium for two months or more.

3. The process according to claim 1, wherein the rat cell is a myeloma cell or a hybrid cell derived from a myeloma cell.

4. The process according to claim 1, wherein the rat cell is YB2/3HL.P2.G11.16Ag.20 (ATCC CRL 1662).

5. The process according to claim 1, wherein the cell is a cell to which a recombinant DNA comprising DNA encoding the desired polypeptide is introduced.

6. The process according to claim 1, wherein the culturing is carried out by batch culture, fed-batch culture or perfusion culture.

7. The process according to claim 1, comprising adding at least one member selected from the group consisting of a nutrient factor and a physiologically active substance to the medium during the culturing.

8. The process according to claim 7, wherein the nutrient factor is at least one member selected from the group consisting of glucose, an amino acid and a vitamin.

9. The process according to claim 1, wherein the desired polypeptide is an immunologically functional molecule.

10. The process according to claim 9, wherein the immunologically functional molecule is a protein or a peptide.

11. The process according to claim 10, wherein the protein or peptide is an antibody, an antibody fragment or a fusion protein comprising an antibody Fc region.

12. The process according to claim 11, wherein the antibody is an antibody recognizing a tumor-related antigen, an antibody recognizing an allergy- or inflammation-related antigen, an antibody recognizing a circulatory disease-related antigen, an antibody recognizing an autoimmune disease-related antigen, or an antibody recognizing a viral or bacterial infection-related antigen.

13. The process according to claim 12, wherein the antibody recognizing a tumor-related antigen is an anti-GD2 antibody, an anti-GD3 antibody, an anti-GM2 antibody, an anti-HER2 antibody, an anti-CD52 antibody, an anti-MAGE antibody, an anti-basic fibroblast growth factor antibody, an anti-basic fibroblast growth factor receptor antibody, an anti-FGF8 antibody, an anti-FGF8 receptor antibody, an anti-insulin-like growth factor antibody, an anti-PMSA antibody, an anti-vascular endothelial cell growth factor antibody, or an anti-vascular endothelial cell growth factor receptor antibody; the antibody recognizing an allergy- or inflammation-related antigen is an anti-interleukin 6 antibody, an anti-interleukin 6 receptor antibody, an anti-interleukin 5 antibody, an anti-interleukin 5 receptor antibody, an anti-interleukin 4 antibody, an anti-interleukin 4 receptor antibody, an anti-tumor necrosis factor antibody, an anti-tumor necrosis factor receptor antibody, an anti-CCR4 antibody, an anti-chemokine antibody, or an anti-chemokine receptor antibody; the antibody recognizing a circulatory disease-related antigen is an anti-GpIIb/IIIa antibody, an anti-platelet-derived growth factor antibody, an anti-platelet-derived growth factor receptor antibody, or an anti-blood coagulation factor antibody; the antibody recognizing an autoimmune disease-related antigen is an anti-auto-DNA antibody; and the antibody recognizing a viral or bacterial infection-related antigen is an anti-gp120 antibody, an anti-CD4 antibody, an anti-CCR4 antibody, or an anti-verotoxin antibody.

14. The process according to claim 12, wherein the antibody is an anti-GD3 human chimeric antibody, a humanized anti-interleukin 5 receptor a chain antibody, or an anti-GM2 human CDR-grafted antibody.

15. The process according to claim 1, wherein the rat cell line can be cultured in a serum-free medium such that 90% or more of the cells of the original culture remain viable throughout said culturing.

16. The process of claim 1 wherein said culturing of step (b) comprises culturing the rat cell line in a serum-free medium while an insulin concentration in the culture is maintained at 20 mg/l or above, followed by culturing while an insulin concentration in the culture is maintained at 10 mg/l or below.

17. The process of claim 1 wherein said culturing of step (b) comprises culturing the rat cell line in a serum-free medium while an insulin concentration in the culture is maintained at 10 mg/l or above, followed by culturing while an insulin concentration in the culture is maintained at 10 mg/l or below.

18. The process of claim 1 wherein said culturing of step (b) comprises culturing the rat cell line in a serum-free medium while an insulin concentration in the culture is maintained at 10 mg/l or above, followed by culturing while an insulin concentration in the culture is maintained at 5 mg/l or below.

* * * * *